United States Patent
Pegington et al.

(10) Patent No.: US 10,434,102 B2
(45) Date of Patent: Oct. 8, 2019

(54) ORGANIC LIGHT EMITTING DEVICE

(71) Applicants: Sumitomo Chemical Company Limited, Tokyo (JP); Cambridge Display Technology Limited, Cambridgeshire (GB)

(72) Inventors: Ruth Pegington, Godmanchester (GB); Martin Humphries, Godmanchester (GB)

(73) Assignees: Sumitomo Chemical Company Limited, Tokyo (JP); Cambridge Display Technology Limited, Godmanchester (GB)

( * ) Notice: Subject to any disclaimer, the term of this patent is extended or adjusted under 35 U.S.C. 154(b) by 0 days.

(21) Appl. No.: 15/819,884

(22) Filed: Nov. 21, 2017

(65) Prior Publication Data

US 2018/0078554 A1    Mar. 22, 2018

Related U.S. Application Data

(62) Division of application No. 14/919,460, filed on Oct. 21, 2015, now Pat. No. 9,859,498.

(30) Foreign Application Priority Data

Oct. 23, 2014 (GB) .................................. 1418876.7

(51) Int. Cl.
| | | |
|---|---|---|
| *C07D 401/06* | (2006.01) | |
| *A61K 31/517* | (2006.01) | |
| *H01L 51/00* | (2006.01) | |
| *C08G 61/12* | (2006.01) | |
| *C07D 401/14* | (2006.01) | |
| *C07D 417/14* | (2006.01) | |
| *H01L 51/50* | (2006.01) | |
| *H01L 51/56* | (2006.01) | |

(52) U.S. Cl.
CPC .......... *A61K 31/517* (2013.01); *C07D 401/06* (2013.01); *C07D 401/14* (2013.01); *C07D 417/14* (2013.01); *C08G 61/12* (2013.01); *H01L 51/00* (2013.01); *H01L 51/0039* (2013.01); *H01L 51/0043* (2013.01); *H01L 51/0095* (2013.01); *C08G 2261/12* (2013.01); *C08G 2261/228* (2013.01); *C08G 2261/3142* (2013.01); *C08G 2261/3162* (2013.01); *C08G 2261/418* (2013.01); *C08G 2261/512* (2013.01); *C08G 2261/71* (2013.01); *C08G 2261/95* (2013.01); *H01L 51/5004* (2013.01); *H01L 51/5056* (2013.01); *H01L 51/56* (2013.01); *H01L 2251/308* (2013.01)

(58) Field of Classification Search
CPC .................................................... A61K 31/517
See application file for complete search history.

(56) References Cited

U.S. PATENT DOCUMENTS

| | | | |
|---|---|---|---|
| 8,343,381 B1 * | 1/2013 | Chesterfield | C08G 61/12 252/500 |
| 2005/0147846 A1 | 7/2005 | Marks et al. | |
| 2011/0198573 A1 * | 8/2011 | Iida | C08G 61/12 257/40 |
| 2012/0007072 A1 | 1/2012 | Murota et al. | |
| 2016/0126461 A1 | 5/2016 | Pegington et al. | |

FOREIGN PATENT DOCUMENTS

| | | |
|---|---|---|
| GB | 2 466 843 A | 7/2010 |
| GB | 2 484 680 A | 4/2012 |
| JP | 2012-146811 A | 8/2012 |

OTHER PUBLICATIONS

U.S. Appl. No. 14/919,460, filed Oct. 21, 2015, Pegington et al.
GB1418876.7, Sep. 30, 2015, Combined Search and Examination Report.
Combined Search and Examination Report for Great Britain Application No. 1418876.7, dated Sep. 30, 2015, pp. 1-7.

* cited by examiner

*Primary Examiner* — Paul V Ward
(74) *Attorney, Agent, or Firm* — Wolf, Greenfield & Sacks, P.C.

(57) ABSTRACT

An OLED comprising a hole-transporting layer and light-emitting layer wherein the hole-transporting layer comprises a hole-transporting polymer wherein no more than 5% of the polystyrene equivalent polymer weight measured by gel permeation chromatography consists of chains with weight of less than 50,000.

22 Claims, 4 Drawing Sheets

ORGANIC LIGHT EMITTING DEVICE

RELATED APPLICATIONS

This is a divisional patent application of U.S. application Ser. No. 14/919,460, filed Oct. 21, 2015, which claims priority under 35 U.S.C. § 119(a)-(d) or 365(b) to British application number 1418876.7, filed Oct. 23, 2014; the entire contents of each is herein incorporated by reference.

BACKGROUND

Electronic devices containing active organic materials are attracting increasing attention for use in devices such as organic light emitting diodes (OLEDs), organic photoresponsive devices (in particular organic photovoltaic devices and organic photosensors), organic transistors and memory array devices. Devices containing active organic materials offer benefits such as low weight, low power consumption and flexibility. Moreover, use of soluble organic materials allows use of solution processing in device manufacture, for example inkjet printing or spin-coating.

An OLED may comprise a substrate carrying an anode, a cathode and one or more organic light-emitting layers between the anode and cathode.

Holes are injected into the device through the anode and electrons are injected through the cathode during operation of the device. Holes in the highest occupied molecular orbital (HOMO) and electrons in the lowest unoccupied molecular orbital (LUMO) of a light-emitting material combine to form an exciton that releases its energy as light.

Suitable light-emitting materials include small molecule, polymeric and dendrimeric materials. Suitable light-emitting polymers include poly(arylene vinylenes) such as poly (p-phenylene vinylenes) and polyarylenes such as polyfluorenes.

A light emitting layer may comprise a semiconducting host material and a light-emitting dopant wherein energy is transferred from the host material to the light-emitting dopant. For example, J. Appl. Phys. 65, 3610, 1989 discloses a host material doped with a fluorescent light-emitting dopant (that is, a light-emitting material in which light is emitted via decay of a singlet exciton).

Phosphorescent dopants are also known (that is, a light-emitting dopant in which light is emitted via decay of a triplet exciton).

US 2011/0198573 describes hole-transporting polymers with crosslinkable groups.

JP 2007/204721 describes a method of fractionating an organic polymer material by bringing the organic polymer material into contact with porous particles.

It is an aim of the present invention to provide an OLED device with an improved properties for instance an improved device lifetime.

SUMMARY OF THE INVENTION

A first aspect of the present invention provides an OLED comprising a hole-transporting layer and light-emitting layer wherein the hole-transporting layer comprises a hole-transporting polymer wherein no more than 5% of the polystyrene equivalent polymer weight measured by gel permeation chromatography consists of chains with a molecular weight of less than 50,000.

A second aspect of the present invention provides an OLED comprising a hole-transporting layer and light-emitting layer wherein the hole-transporting layer comprises a hole-transporting polymer having no more than 10% of the polystyrene equivalent polymer weight measured by gel permeation chromatography consists of chains with a molecular weight of less than 100,000.

In a third aspect the invention provides an OLED comprising a hole-transporting layer and light-emitting layer wherein the hole-transporting layer comprises a hole-transporting polymer wherein no more than 5% of the weight of the polymer consists of polymer chains with a p/r ratio of less than about 100 wherein p/r is absolute polymer chain weight/average repeat unit weight.

A fourth aspect of the present invention provides a process for the preparation of an OLED according to the first or second or third aspect of the invention, comprising the steps of:

(i) forming a hole-transporting layer which comprises a hole-transporting polymer; and (ii) forming a light-emitting layer over the hole transporting layer wherein the light-emitting layer is formed by depositing a formulation comprising the material or materials of said layer and at least one solvent and evaporating the at least one solvent.

In a fifth aspect the invention provides a method of forming a fractionated hole-transporting polymer comprising the step of separating a low molecular weight fraction from a hole-transporting polymer.

The fractionated hole-transporting polymer of the fifth aspect may be as described in any of the first, second and third aspects of the invention.

As used herein, "molecular weight" is a weight in Daltons.

As used herein, "absolute polymer chain molecular weight" is an absolute molecular weight of a polymer chain as measured by triple detection gel permeation chromatography.

As used herein, "average repeat unit weight" is the mean average molecular mass in Daltons of repeat units of the polymer determined from the weights of monomers used to form the polymer and, in the case of a polymer comprising two or more repeat units having different weights, the proportions of the monomers.

A percentage of the polymer weight for a given molecular weight range as described herein is the normalised cumulative height of the polymer weight distribution for that molecular weight range.

DESCRIPTION OF THE DRAWINGS

The invention will now be described in more detail with reference to the drawings in which.

DETAILED DESCRIPTION

Figure 1:
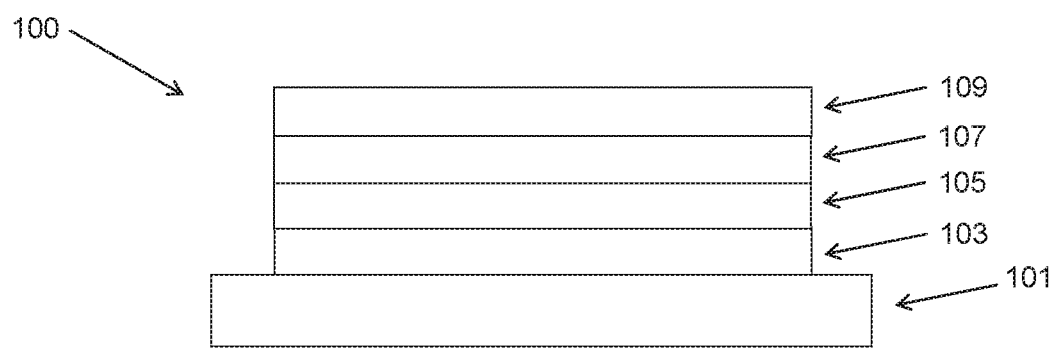
FIG. 1 illustrates schematically an OLED according to an embodiment of the invention.

With reference to FIG. 1, an OLED 100 according to an embodiment of the invention has an anode 101, a cathode 107, a light-emitting layer 105 between the anode and the cathode, and a hole-transporting layer 103 between the anode 101 and the light-emitting layer 105. The device is supported on a substrate 109, which may be a glass or plastic substrate.

One or more further layers may be provided between the anode and the cathode, for example a hole-injection layer, an electron-blocking layer, an electron-transporting layer or an electron blocking layer. In a preferred embodiment, a hole-injection layer is provided between the anode and the hole-transporting layer. Where present, the hole-injection layer is preferably adjacent to the hole-transporting layer. Preferably, the hole-transporting layer is adjacent to the light-emitting layer.

Light-emitting layer 105 may contain one or more fluorescent light-emitting materials, one or more phosphorescent light-emitting materials or a combination of at least one fluorescent light-emitting material and at least one phosphorescent light-emitting material.

The OLED may contain more than one light-emitting layer, for example a plurality of light-emitting layers that together produce white light.

Exemplary OLED layer structures include the following:
Anode/Hole transporting layer/Light-emitting layer/Cathode
Anode/Hole-injection layer/Hole-transporting layer/Light-emitting layer/Cathode
Anode/Hole-injection layer/Hole-transporting layer/Light-emitting layer/Electron-transporting layer/Cathode.

A first aspect of the present invention provides an OLED comprising a hole-transporting layer and light-emitting layer wherein the hole-transporting layer comprises a hole-transporting polymer wherein no more than 5% of the polystyrene equivalent polymer weight measured by gel permeation chromatography consists of chains with a molecular weight of less than 50,000.

In a preferred embodiment of the first aspect of the invention, the hole-transporting layer comprises a hole-transporting polymer wherein no more than 1% of the polystyrene equivalent polymer weight measured by gel permeation chromatography consists of polymer chains with a molecular weight of less than 50,000. Most preferably the hole-transporting layer comprises a hole-transporting polymer wherein less than 0.5% or less than 0.2% or less than 0.1% of the polystyrene equivalent polymer weight measured by gel permeation chromatography consists of polymer chains with a molecular weight of less than 50,000.

In a preferred embodiment of the first aspect of the invention, the hole transporting layer comprises a hole transporting polymer wherein no more than 10% of the polystyrene equivalent polymer weight measured by gel permeation chromatography consists of polymer chains with a molecular weight of less than 100,000. Preferably the hole-transporting layer comprises a hole-transporting polymer wherein no more than 5%, 4%, 3%, 2% or 1% of the polystyrene equivalent polymer weight measured by gel permeation chromatography consists of polymer chains with a molecular weight of less than 100,000.

A second aspect of the present invention provides an OLED comprising a hole-transporting layer and light-emitting layer wherein the hole-transporting layer comprises a hole-transporting polymer wherein no more than 10% of the polystyrene equivalent polymer weight measured by gel permeation chromatography consists of polymer chains with a molecular weight of less than 100,000.

In a preferred embodiment of the second aspect of the invention, the hole transporting layer comprises a hole transporting polymer wherein no more than 5% of the polystyrene equivalent polymer weight measured by gel permeation chromatography consists of polymer chains with a molecular weight of less than 100,000. Preferably the hole-transporting layer comprises a hole-transporting polymer wherein no more than 4%, 3%, 2% or 1% of the polystyrene equivalent polymer weight measured by gel permeation chromatography consists of polymer chains with a molecular weight of less than 100,000.

In a preferred embodiment of the first and second aspects of the invention, more than 20%, optionally more than 25%, of the polystyrene equivalent polymer weight measured by gel permeation chromatography consists of polymer chains with a molecular weight of at least 300,000.

In a third aspect the invention provides an OLED comprising a hole-transporting layer and light-emitting layer wherein the hole-transporting layer comprises a hole-transporting polymer wherein no more than 5% of the weight of the polymer as measured by triple detection gel permeation chromatography consists of polymer chains with a p/r ratio of less than about 50 wherein p/r is absolute polymer chain molecular weight/average repeat unit molecular weight.

In a preferred embodiment of the third aspect, less than 4%, less than 3%, less than 2% or less than 1% of the weight of the polymer as measured by triple detection gel permeation chromatography consists of polymer chains with a p/r ratio of less than about 50.

In a preferred embodiment of the third aspect, less than 10%, less than 5%, less than 4%, less than 3%, less than 2% or less than 1% of the weight of the polymer as measured by triple detection gel permeation chromatography consists of polymer chains with a p/r ratio of less than about 100, preferably less than about 150.

In a preferred embodiment of the third aspect, more than 20%, optionally more than 25% of the weight of the polymer as measured by triple detection gel permeation chromatography consists of polymer chains with a p/r ratio of more than about 500.

In a preferred embodiment of the first, second or third aspect of the invention, the hole-transporting layer comprises a hole-transporting polymer having a polydispersity index of less than 4, preferably less than 3 or 2, most preferably about 1.5.

As used herein 'polydispersity index' refers to a polystyrene equivalent dispersity index as measured by gel permeation chromatography.

In a preferred embodiment of the first, second or third aspect of the invention, the hole-transporting layer comprises a hole-transporting polymer having a number-average molecular weight (Mn) in the range of $5 \times 10^4$, optionally $1 \times 10^5$ up to $5 \times 10^5$, and preferably in the range of $2 \times 10^5$ to $5 \times 10^5$.

As used herein 'number-average molecular weight' refers to polystyrene equivalent number-average molecular weight as measured by gel permeation chromatography.

In a preferred embodiment of the first, second or third aspect of the invention, the hole-transporting layer comprises a hole-transporting polymer having a polystyrene equivalent weight average molecular weight as measured by gel permeation chromatography is in the range of 70,000 or $1 \times 10^5$ up to $1 \times 10^6$, and preferably $2 \times 10^5$ to $5 \times 10^5$.

The hole-transporting layer may consist essentially of the hole-transporting polymer or may comprise one or more further materials mixed with the hole-transporting polymer, for example one or more light-emitting materials.

A fourth aspect of the invention provides a process for the preparation of an OLED according to the first, second or third aspect of the invention, comprising the steps of:
(i) forming a hole-transporting layer which comprises a hole-transporting polymer; and
(ii) forming a light-emitting layer over the hole-transporting layer wherein the light-emitting layer is formed by depositing a formulation comprising the material or materials of said layer and at least one solvent and evaporating the at least one solvent.

In a preferred embodiment of the fourth aspect of the invention, the hole-transporting layer is formed by depositing a formulation comprising the material or materials of said layer and at least one solvent and evaporating the at least one solvent. The hole-transporting polymer may be soluble in one or more solvents used in step (ii) in forming the light-emitting layer. Exemplary solvents that may be used to form the hole-transporting layer and/or the light-emitting layer, either alone or in combination, include substituted benzenes, for example benzene substituted with one or more $C_{1-10}$ alkyl or $C_{1-10}$ alkoxy groups such as toluene, xylene or anisole and mixtures thereof; benzene substituted with one or more chlorine groups; and tetrahydrofuran.

In a preferred embodiment of the fourth aspect of the invention, the hole-transporting layer is crosslinked prior to formation of the light-emitting layer. Preferably, the hole-transporting polymer is crosslinked by thermal treatment or by irradiation. Preferably, the hole-transporting polymer is crosslinked by thermal treatment. Thermal crosslinking may be at a temperature in the range of about 80-250° C., optionally about 80-200° C. or about 130-200° C.

The hole-transporting polymer preferably comprises one or more repeat units substituted with a cross-linkable group. Preferably at least 1 mol % of the repeat units of the polymer comprise a crosslinkable group. More preferably at least 2, 3, 4, 5, 6, 7, 8 or 9 mol % of the repeat units comprise a crosslinkable group. Most preferably at least 10 mol % of the repeat units comprise a crosslinkable group. Preferably, no more than 25 mol % or no more than 20 mol % of the repeat units comprise a crosslinkable group.

A crosslinkable group is a group that may be crosslinked following deposition of a polymer to form a crosslinked layer prior to formation of a subsequent layer. For example the hole-transporting polymer may be crosslinked following deposition to form a crosslinked hole-transporting layer prior to formation a subsequent layer which is typically the light-emitting layer. Crosslinking can reduce the solubility of the polymer in a solvent. Crosslinkable groups may be provided as substituents of any repeat units of the polymer. End groups of the polymer may be substituted with a crosslinkable group in addition to or as an alternative to crosslinkable groups provided as substituents of repeat units. Crosslinkable groups may be selected from:

an arylcyclobutene of formula (III):

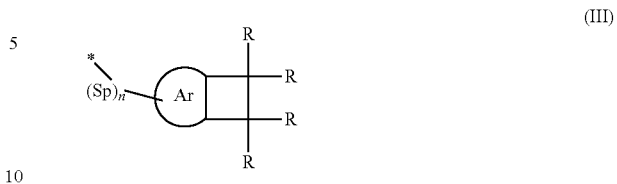

wherein Sp is a spacer group, Ar is an aryl or heteroaryl group that may be unsubstituted or substituted with one or more substituents; n=0 or 1, R independently in each occurrence is selected from H or a substituent and * is a point of attachment of the group of formula (III) to a polymeric repeat unit or end group;
or
a group of formula (IV):

wherein Sp is a spacer group, n=0 or 1, R independently in each occurrence is H or a substituent, and * is a point of attachment of the group of formula (IV) to a polymeric repeat unit or end group.

Preferably, each R is selected from H and $C_{1-20}$ hydrocarbyl. Exemplary hydrocarbyl groups are $C_{1-10}$ alkyl; phenyl; and phenyl substituted with one or more $C_{1-10}$ alkyl groups.

Preferably, R groups of formula (IV) are H.

Preferably, R groups of formula (III) are H or $C_{1-10}$ alkyl.

Preferably, Ar of formula (III) is benzene which may be unsubstituted or substituted, for example substituted with one or more $C_{1-10}$ alkyl groups.

Sp of formula (III) or (IV), if present, may be a $C_{1-20}$ alkyl group wherein one or more non-adjacent C atoms are replaced with optionally substituted aryl or heteroaryl, O, S, C=O or —COO—, and one or more H atoms may be replaced with F. Exemplary spacer groups are alkyl, alkoxy, phenylalkyl.

The hole-transporting polymer of the first, second or third aspect may be a conjugated polymer comprising repeat units in the polymer backbone that are conjugated together, or may be a non-conjugated polymer.

Preferably, the hole-transporting polymer is a conjugated polymer. Preferably, the conjugated polymer comprises repeat units comprising arylene groups that are conjugated to arylene groups of adjacent repeat units.

Exemplary hole-transporting polymers comprise a group of formula (V):

wherein $Ar^8$ and $Ar^9$ in each occurrence are independently selected from substituted or unsubstituted aryl or heteroaryl, g is greater than or equal to 1, preferably 1 or 2, $R^{13}$ is H, a substituent or a bond to a polymer backbone, and c and d are each independently 1, 2 or 3.

$R^{13}$, which may be the same or different in each occurrence when g>1, is preferably a substituent and is more preferably selected from the group consisting of alkyl, for example $C_{1-20}$ alkyl, $Ar^{10}$, or a branched or linear chain of $Ar^{10}$ groups, wherein $Ar^{10}$ in each occurrence is independently optionally substituted aryl or heteroaryl. Exemplary groups $R^{13}$ are $C_{1-20}$ alkyl, phenyl and phenyl substituted with one or more $C_{1-20}$ alkyl groups.

Any of $Ar^8$, $Ar^9$ and, if present, $Ar^{10}$ bound directly to a N atom in the repeat unit of formula (V) may be linked by a direct bond or a divalent linking atom or group to another of $Ar^8$, $Ar^9$ and $Ar^{10}$ bound directly to the same N atom. Preferred divalent linking atoms and groups include O, S; substituted N; and substituted C.

Any of $Ar^8$, $Ar^9$ and, if present, $Ar^{10}$ may be substituted with one or more substituents. Exemplary substituents are substituents $R^{14}$, wherein each $R^{14}$ may independently be selected from the group consisting of substituted or unsubstituted alkyl, optionally $C_{1-20}$ alkyl, wherein one or more non-adjacent C atoms may be replaced with optionally substituted aryl or heteroaryl, O, S, substituted N, C=O or —COO— and one or more H atoms may be replaced with F.

Substituted N or substituted C, where present, may be N or C substituted with a hydrocarbyl group (in the case of substituted N) or two hydrocarbyl groups (in the case of substituted C), for example a $C_{1-10}$ alkyl, unsubstituted phenyl or phenyl substituted with one or more $C_{1-10}$ alkyl groups.

A group of formula (V) may be provided in the main chain of a conjugated polymer in which case it may be a repeat unit of formula (Va):

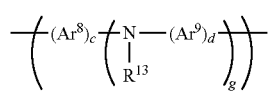

(Va)

wherein $Ar^8$, $Ar^9$, $R^{13}$, c and d are as defined above for formula (V).

A group of formula (V) may be a side-group of a conjugated or non-conjugated polymer comprising repeat units of formula (VII):

(Formula V)

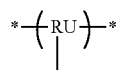

(VII)

wherein RU is a backbone repeat unit, for example a homopolymer consisting of or a copolymer comprising repeat units of formula group of formula (VIIa):

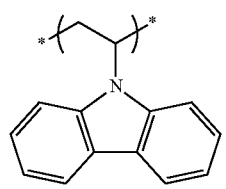

(VIIa)

Preferred repeat units of formula (Va) have sub-formulae 1-3:

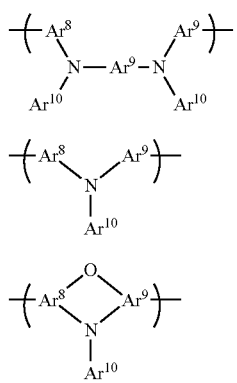

Preferably, $Ar^8$ and $Ar^{10}$ of repeat units of formula 1 are phenyl and $Ar^9$ is phenyl or a polycyclic aromatic group. More preferably $Ar^9$, most preferably the central $Ar^9$ group of formula 1 bound directly to two N atoms is a $C_{10-20}$ polycyclic aromatic, optionally an optionally substituted fluorene, for example as described in WO 2005/049546 and WO 2013/108022 the contents of which are incorporated by reference.

In one preferred arrangement, $R^{13}$ is $Ar^{10}$ and each of $Ar^8$, $Ar^9$ and $Ar^{10}$ are independently unsubstituted or substituted with one or more $C_{1-20}$ alkyl groups.

In a preferred arrangement, $Ar^8$, $Ar^9$ and $Ar^{10}$ are phenyl, each of which may independently be substituted with one or more substituents as described above.

In another preferred arrangement, $Ar^8$ and $Ar^9$ are phenyl, each of which may be substituted with one or more $C_{1-20}$ alkyl groups, and $R^{13}$ is 3,5-diphenylbenzene wherein each phenyl may be substituted with one or more $C_{1-20}$ alkyl groups.

In another preferred arrangement, c, d and g are each 1 and $Ar^8$ and $Ar^9$ are phenyl linked by an oxygen atom to form a phenoxazine ring.

Amine repeat units may be provided in a molar amount in the range of about 0.5 mol % up to about 50 mol %, optionally up to 40 mol %.

Hole-transporting polymers as described herein may be homopolymers, for example homopolymers of a repeat unit comprising a group of formula (V), or may be copolymers comprising one or more co-repeat units.

Exemplary co-repeat units include arylene repeat units, for example 1,2-, 1,3- and 1,4-phenylene repeat units, 3,6- and 2,7-linked fluorene repeat units, indenofluorene, naphthalene, anthracene and phenanthrene repeat units, each of which may be unsubstituted or substituted with one or more substituents. Substituents may be selected from groups $R^7$ described below.

One preferred class of arylene repeat units is phenylene repeat units, such as phenylene repeat units of formula (X):

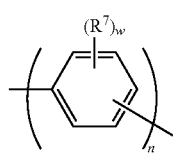

(X)

wherein w in each occurrence is independently 0, 1, 2, 3 or 4, optionally 1 or 2; n is 1, 2 or 3; and $R^7$ independently in each occurrence is a substituent.

Where present, each $R^7$ may independently be selected from the group consisting of:
- alkyl, optionally $C_{1-20}$ alkyl, wherein one or more non-adjacent C atoms may be replaced with optionally substituted aryl or heteroaryl, O, S, substituted N, C=O or —COO—, and one or more H atoms may be replaced with F;
- aryl and heteroaryl groups that may be unsubstituted or substituted with one or more substituents, preferably phenyl substituted with one or more $C_{1-20}$ alkyl groups;
- a linear or branched chain of aryl or heteroaryl groups, each of which groups may independently be substituted, for example a group of formula $—(Ar^3)_r$ wherein each $Ar^3$ is independently an aryl or heteroaryl group and r is at least 2, preferably a branched or linear chain of phenyl groups each of which may be unsubstituted or substituted with one or more $C_{1-20}$ alkyl groups; and
- a crosslinkable-group, for example a group, optionally a group of formula (III) or (IV).

Substituted N, where present, may be $—NR^2—$ wherein $R^2$ is $C_{1-20}$ alkyl; unsubstituted phenyl; or phenyl substituted with one or more $C_{1-20}$ alkyl groups.

Preferably, each $R^7$ is independently selected from $C_{1-40}$ hydrocarbyl, and is more preferably selected from $C_{1-20}$ alkyl; unsubstituted phenyl; and phenyl substituted with one or more $C_{1-20}$ alkyl groups; a linear or branched chain of phenyl groups, wherein each phenyl may be unsubstituted or substituted with one or more substituents; and a crosslinkable group.

If n is 1 then exemplary repeat units of formula (X) include the following:

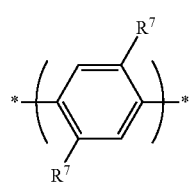

A particularly preferred repeat unit of formula (X) has formula (Xa):

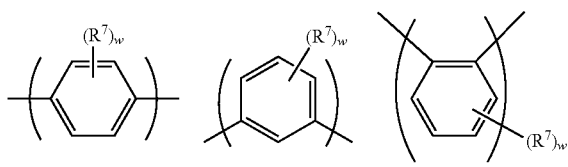

(Xa)

Substituents $R^7$ of formula (Xa) are adjacent to linking positions of the repeat unit, which may cause steric hindrance between the repeat unit of formula (Xa) and adjacent repeat units, resulting in the repeat unit of formula (Xa) twisting out of plane relative to one or both adjacent repeat units.

Exemplary repeat units where n is 2 or 3 include the following:

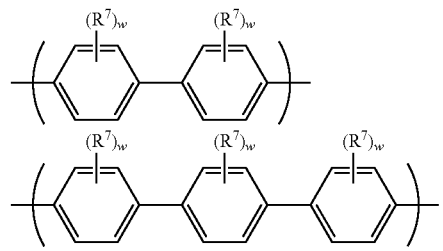

A preferred repeat unit has formula (Xb):

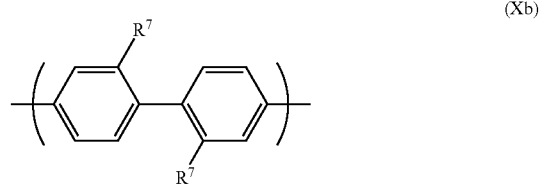

(Xb)

The two $R^7$ groups of formula (Xb) may cause steric hindrance between the phenyl rings they are bound to, resulting in twisting of the two phenyl rings relative to one another.

A further class of arylene repeat units is optionally substituted fluorene repeat units, such as repeat units of formula (XI):

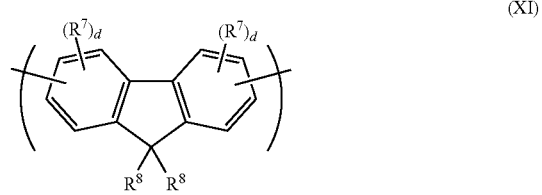

(XI)

wherein $R^8$ in each occurrence is the same or different and is a substituent wherein the two groups $R^8$ may be linked to form a ring; $R^7$ is a substituent as described above; and d is 0, 1, 2 or 3.

Each $R^8$ may independently be selected from the group consisting of:
- alkyl, optionally $C_{1-20}$ alkyl, wherein one or more non-adjacent C atoms may be replaced with optionally substituted aryl or heteroaryl, O, S, substituted N, C=O or —COO—, and one or more H atoms may be replaced with F;
- aryl and heteroaryl groups that may be unsubstituted or substituted with one or more substituents, preferably phenyl substituted with one or more $C_{1-20}$ alkyl groups; and
- a linear or branched chain of aryl or heteroaryl groups, each of which groups may independently be substituted, for example a group of formula $—(Ar^7)_r$ wherein each $Ar^7$ is independently an aryl or heteroaryl group and r is at least 2, optionally 2 or 3, preferably a branched or linear chain of phenyl groups each of which may be unsubstituted or substituted with one or more $C_{1-20}$ alkyl groups.
- a crosslinkable-group, optionally a group of formula (III) or (IV).

Preferably, each $R^8$ is independently a $C_{1-40}$ hydrocarbyl group.

Different groups $R^8$ are disclosed in WO 2012/104579 the contents of which are incorporated in entirety by reference.

Substituted N, where present, may be —$NR^2$— wherein $R^2$ is as described above.

Exemplary substituents $R^7$ are alkyl, for example $C_{1-20}$ alkyl, wherein one or more non-adjacent C atoms may be replaced with O, S, C=O and —COO—, optionally substituted aryl, optionally substituted heteroaryl, alkoxy, alkylthio, fluorine, cyano and arylalkyl. Particularly preferred substituents include $C_{1-20}$ alkyl and substituted or unsubstituted aryl, for example phenyl. Optional substituents for the aryl include one or more $C_{1-20}$ alkyl groups.

The extent of conjugation of repeat units of formula (XI) to aryl or heteroaryl groups of adjacent repeat units in the polymer backbone may be controlled by (a) linking the repeat unit through the 3- and/or 6-positions to limit the extent of conjugation across the repeat unit, and/or (b) substituting the repeat unit with one or more substituents $R^8$ in or more positions adjacent to the linking positions in order to create a twist with the adjacent repeat unit or units, for example a 2,7-linked fluorene carrying a $C_{1-20}$ alkyl substituent in one or both of the 3- and 6-positions.

The repeat unit of formula (XI) may be a 2,7-linked repeat unit of formula (XIa):

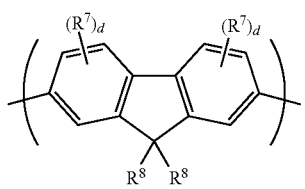

(XIa)

Optionally, the repeat unit of formula (XIa) is not substituted in a position adjacent to the 2- or 7-position. A relatively high degree of conjugation across the repeat unit of formula (XIa) may be provided in the case where each d=0, or where any substituent $R^7$ is not present at a position adjacent to the linking 2- or 7-positions of formula (XIa).

Conjugation across the repeat unit of formula (XIa) may be limited in the case where at least one d is at least 1, and where at least one substituent $R^7$ is present at a position adjacent to the linking 2- or 7-positions of formula (XIa). Optionally, each d is 1 and the 3- and/or 6-position of the repeat unit of formula (XIa) is substituted with a substituent $R^7$ to provide a relatively low degree of conjugation across the repeat unit. Substitutions at the 3- and/or 6-positions is disclosed in WO 2013/191086 the contents of which are incorporated herein by reference.

The repeat unit of formula (XI) may be a 3,6-linked repeat unit of formula (XIb)

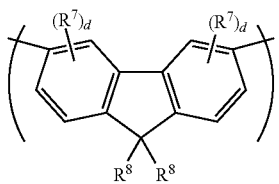

(XIb)

The extent of conjugation across a repeat unit of formula (XIb) may be relatively low as compared to a corresponding repeat unit of formula (XIa).

Another exemplary arylene repeat unit has formula (VIII):

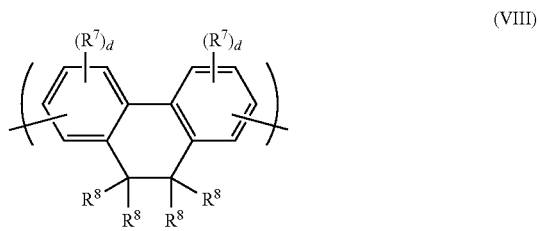

(VIII)

wherein $R^7$, $R^8$ and d are as described with reference to formulae (X) and (XI) above. Any of the $R^7$ groups may be linked to any other of the $R^7$ groups to form a ring. The ring so formed may be unsubstituted or may be substituted with one or more substituents, optionally one or more $C_{1-20}$ alkyl groups.

Repeat units of formula (VIII) may have formula (VIIIa) or (VIIIb):

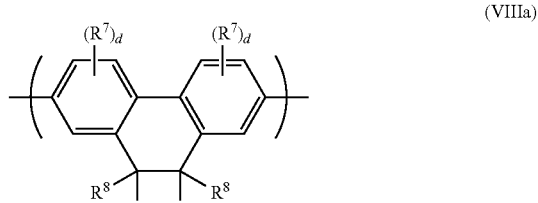

(VIIIa)

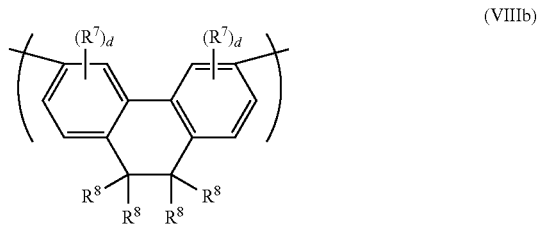

(VIIIb)

The one or more co-repeat units may include a conjugation-breaking repeat unit, which is a repeat unit that does not provide any conjugation path between repeat units adjacent to the conjugation-breaking repeat unit.

Polymers as described herein are suitably amorphous

Polymer Synthesis

One method of forming conjugated hole-transporting polymers as described herein is Suzuki polymerisation, for example as described in WO 00/53656 or U.S. Pat. No. 5,777,070 which allows formation of C—C bonds between two aromatic or heteroaromatic groups, and so enables formation of polymers having conjugation extending across two or more repeat units. Suzuki polymerisation takes place in the presence of a palladium complex catalyst and a base.

As illustrated in Scheme 1, in the Suzuki polymerisation process a monomer for forming repeat units RU1 has two leaving groups LG1 such as boronic acid or boronic ester group bound to the same or different arylene or heteroarylene groups of RU1, and a monomer for forming repeat units RU2 has two leaving groups LG2 such as halogen, sulfonic acid or sulfonic ester bound to the same or different arylene or heteroarylene groups of RU1. The monomers are polymerised to form a carbon-carbon bond between arylene or heteroarylene groups of RU 1 and RU 2:

Scheme 1

nLG1-RU1-LG1 + nLG2-RU2-LG2 ⟶ -(RU1-RU2)$_n$-

Exemplary boronic esters have formula (VI):

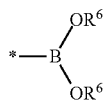

(VI)

wherein $R^6$ in each occurrence is independently a $C_{1-20}$ alkyl group, * represents the point of attachment of the boronic ester to an aromatic ring of the monomer, and the two groups $R^6$ may be linked to form a ring. In a preferred embodiment, the two groups $R^6$ are linked to form the pinacol ester of boronic acid:

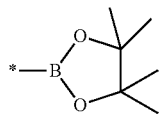

It will be understood by the skilled person that a monomer LG1-RU1-LG1 will not polymerise to form a direct carbon-carbon bond with another monomer LG1-RU1-LG1. A monomer LG2-RU2-LG2 will not polymerise to form a direct carbon-carbon bond with another monomer LG2-RU2-LG2.

Preferably, one of LG1 and LG2 is bromine or iodine and the other is a boronic acid or boronic ester.

This selectivity means that the ordering of repeat units in the polymer backbone can be controlled such that all or substantially all RU1 repeat units formed by polymerisation of LG1-RU1-LG1 are adjacent, on both sides, to RU2 repeat units.

In the example of Scheme 1 above, an AB copolymer is formed by copolymerisation of two monomers in a 1:1 ratio, however it will be appreciated that more than two or more than two monomers may be used in the polymerisation, and any ratio of monomers may be used.

In the example of Scheme 1 above, a linear copolymer is formed. In other embodiments, one or more monomers may contain 3 or more leaving groups to form a branching polymer.

The base may be an organic or inorganic base. Exemplary organic bases include tetra-alkylammonium hydroxides, carbonates and bicarbonates. Exemplary inorganic bases include metal (for example alkali or alkali earth) hydroxides, carbonates and bicarbonates.

The palladium complex catalyst may be a palladium (0) or palladium (II) compound.

Particularly preferred catalysts are tetrakis(triphenylphosphine)palladium (0) and palladium (II) acetate mixed with a phosphine.

A phosphine may be provided, either as a ligand of the palladium compound catalyst or as a separate compound added to the polymerisation mixture. Exemplary phosphines include triarylphosphines, for example triphenylphosphines wherein each phenyl may independently be unsubstituted or substituted with one or more substituents, for example one or more $C_{1-5}$ alkyl or $C_{1-5}$ alkoxy groups.

Particularly preferred are triphenylphospine and tris(ortho-methoxytriphenyl) phospine.

A further polymerisation method is Yamamoto polymerisation in which monomers carrying halogen (preferably bromine) leaving groups react in the presence of a nickel catalyst.

The polymerisation reaction may take place in a single organic liquid phase in which all components of the reaction mixture are soluble. The reaction may take place in a two-phase aqueous-organic system, in which case a phase transfer agent may be used. The reaction may take place in an emulsion formed by mixing a two-phase aqueous-organic system with an emulsifier.

The polymer may be end-capped by addition of an endcapping reactant. Suitable end-capping reactants are aromatic or heteroaromatic materials substituted with only one leaving group. The end-capping reactants may include reactants substituted with a halogen for reaction with a boronic acid or boronic ester group at a polymer chain end, and reactants substituted with a boronic acid or boronic ester for reaction with a halogen at a polymer chain end. Exemplary end-capping reactants are halobenzenes, for example bromobenzene, and phenylboronic acid. End-capping reactants may be added during or at the end of the polymerisation reaction.

After polymer synthesis the hole-transporting polymer may be modified to provide a polymer having a molecular weight as described in the first or second aspects of the invention.

The polymer molecular weight may be fractionated by filtration through a size exclusion membrane.

Preferred methods of fractionation include selective precipitation or chromatographic methods such as preparative size exclusion chromatography. Most preferably the fractionation is by selective precipitation.

Selective precipitation is a method in which a polymer is dissolved in one or more solvents. A solvent or solvent mixture in which the polymer is less soluble is added to the polymer solution to precipitate the polymer. Higher molecular weight polymer chains are selectively precipitated and therefore the precipitated solid is depleted of lower molecular weight polymer chains.

Light-Emitting Layers

An OLED may contain one or more light-emitting layers. Suitable light-emitting materials for a light-emitting layer include polymeric, small molecule and dendrimeric light-emitting materials, each of which may be fluorescent or phosphorescent.

A light-emitting layer of an OLED may be unpatterned, or may be patterned to form discrete pixels. Each pixel may be further divided into subpixels. The light-emitting layer may contain a single light-emitting material, for example for a monochrome display or other monochrome device, or may contain materials emitting different colours, in particular red, green and blue light-emitting materials for a full-colour display.

A light-emitting layer may contain a mixture of more than one light-emitting material, for example a mixture of light-emitting materials that together provide white light emission.

A blue light emitting material may have a photoluminescent spectrum with a peak in the range of 400-490 nm.

A green light emitting material may have a photoluminescent spectrum with a peak in the range of more than 490 nm up to 580 nm.

A red light emitting material may optionally have a peak in its photoluminescent spectrum of more than 580 nm up to 650 nm, preferably 600-630 nm.

Exemplary fluorescent polymeric light-emitting materials include polymers comprising one or more of arylene repeat units, arylene vinylene repeat units and arylamine repeat units. A fluorescent light-emitting layer may consist of a light-emitting material alone or may further comprise one or more further materials mixed with the light-emitting material. Exemplary further materials may be selected from hole-transporting materials; electron-transporting materials and triplet-accepting materials, for example a triplet-accepting polymer as described in WO 2013/114118, the contents of which are incorporated herein by reference.

Preferred light-emitting polymers are copolymers comprising one or more arylene repeat units selected from formulae (X), (XI) and (VIII) and (V) described above with reference to the hole-transporting polymer; phenanthrene repeat units; naphthalene repeat units; anthracene repeat units; and perylene repeat units. Each of these repeat units may be linked to adjacent repeat units through any two of the aromatic carbon atoms of these units. Specific exemplary linkages include 9,10-anthracene; 2,6-anthracene; 1,4-naphthalene; 2,6-naphthalene; 2,7-phenanthrene; and 2,5-perylene. Each of these repeat units may be substituted or unsubstituted, for example substituted with one or more $C_{1-40}$ hydrocarbyl groups.

Exemplary phosphorescent light-emitting materials include metal complexes comprising substituted or unsubstituted complexes of formula (IX):

  (IX)

wherein M is a metal; each of $L^1$, $L^2$ and $L^3$ is a coordinating group; q is an integer; r and s are each independently 0 or an integer; and the sum of (a. q)+(b. r)+(c.s) is equal to the number of coordination sites available on M, wherein a is the number of coordination sites on $L^1$, b is the number of coordination sites on $L^2$ and c is the number of coordination sites on $L^3$. Preferably, a, b and c are each 1 or 2. Preferably, a, b and c are each 2 (bidentate ligands). Preferably, q is 2 or 3 and r and s are 0 or 1.

Heavy elements M induce strong spin-orbit coupling to allow rapid intersystem crossing and emission from triplet or higher states. Suitable heavy metals M include d-block metals, in particular those in rows 2 and 3 i.e. elements 39 to 48 and 72 to 80, in particular ruthenium, rhodium, palladium, rhenium, osmium, iridium, platinum and gold. Iridium is particularly preferred.

Exemplary ligands $L^1$, $L^2$ and $L^3$ include carbon or nitrogen donors such as porphyrin or bidentate ligands of formula (I):

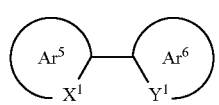 (I)

wherein $Ar^5$ and $Ar^6$ may be the same or different and are independently selected from substituted or unsubstituted aryl or heteroaryl; $X^1$ and $Y^1$ may be the same or different and are independently selected from carbon or nitrogen; and $Ar^5$ and $Ar^6$ may be fused together. Ligands wherein $X^1$ is carbon and $Y^1$ is nitrogen are preferred, in particular ligands in which $Ar^5$ is a single ring or fused heteroaromatic of N and C atoms only, for example pyridyl or isoquinoline, and $Ar^6$ is a single ring or fused aromatic, for example phenyl or naphthyl.

Examples of bidentate ligands are illustrated below:

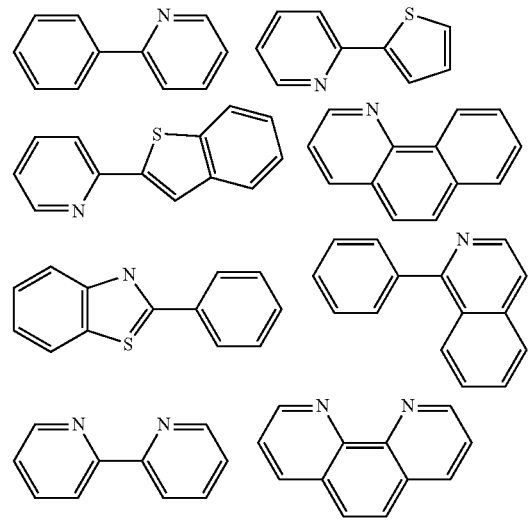

Each of $Ar^5$ and $Ar^6$ may carry one or more substituents. Two or more of these substituents may be linked to form a ring, for example an aromatic ring.

Other ligands suitable for use with d-block elements include diketonates, in particular acetylacetonate (acac); triarylphosphines and pyridine, each of which may be substituted.

Exemplary substituents include groups $R^7$ as described above with reference to Formula (X). Particularly preferred substituents include fluorine or trifluoromethyl which may be used to blue-shift the emission of the complex, for example as disclosed in WO 02/45466, WO 02/44189, US 2002-117662 and US 2002-182441; alkyl or alkoxy groups, for example $C_{1-20}$ alkyl or alkoxy, which may be as disclosed in JP 2002-324679; carbazole which may be used to assist hole transport to the complex when used as an emissive material, for example as disclosed in WO 02/81448; bromine, chlorine or iodine which can serve to functionalise the ligand for attachment of further groups, for example as disclosed in WO 02/68435 and EP 1245659; and dendrons which may be used to obtain or enhance solution processability of the metal complex, for example as disclosed in WO 02/66552.

A light-emitting dendrimer typically comprises a light-emitting core bound to one or more dendrons, wherein each dendron comprises a branching point and two or more dendritic branches. Preferably, the dendron is at least partially conjugated, and at least one of the branching points and dendritic branches comprises an aryl or heteroaryl group, for example a phenyl group. In one arrangement, the branching point group and the branching groups are all phenyl, and each phenyl may independently be substituted with one or more substituents, for example alkyl or alkoxy.

A dendron may have optionally substituted formula (II)

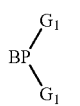
(II)

wherein BP represents a branching point for attachment to a core and $G_1$ represents first generation branching groups.

The dendron may be a first, second, third or higher generation dendron. $G_1$ may be substituted with two or more second generation branching groups $G_2$, and so on, as in optionally substituted formula (IIa):

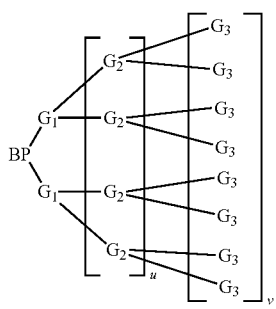
(IIa)

wherein u is 0 or 1; v is 0 if u is 0 or may be 0 or 1 if u is 1; BP represents a branching point for attachment to a core and $G_1$, $G_2$ and $G_3$ represent first, second and third generation dendron branching groups. In one preferred embodiment, each of BP and $G_1$, $G_2$ ... $G_n$ is phenyl, and each phenyl BP, $G_1$, $G_2$ ... $G_{n-1}$ is a 3,5-linked phenyl.

A preferred dendron is a substituted or unsubstituted dendron of formula (IIb):

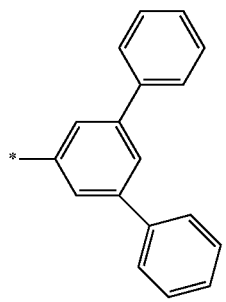
(IIb)

wherein * represents an attachment point of the dendron to a core.

BP and/or any group G may be substituted with one or more substituents, for example one or more $C_{1-20}$ alkyl or alkoxy groups.

Phosphorescent light-emitting materials may be provided in a light-emitting layer with a host material. The host preferably has a triplet energy level that is no more than 0.1 eV lower than that of the phosphorescent light-emitting material, more preferably a triplet energy level that the same as or higher than that of the phosphorescent light-emitting material.

Suitable host materials include small molecule, dendrimeric and polymeric host materials. Polymeric host materials include non-conjugated polymers with pendant charge-transporting groups, for example polyvinylcarbazole, and at least partially conjugated polymers, for example polymers comprising one or both of arylene repeat units and amine repeat units, for example arylene repeat units of formula (X), (XI) and (VIII) and amine repeat units of formula (V).

Phosphorescent light-emitting materials may make up about 0.05 mol % up to about 20 mol %, optionally about 0.1-10 mol % of a host/phosphorescent light-emitting material composition.

The phosphorescent light-emitting material may be physically mixed with the host material or may be covalently bound thereto. In the case of a polymeric host, the phosphorescent light-emitting material may be provided in a side-chain, main chain or end-group of the polymer. Where the phosphorescent material is provided in a polymer side-chain, the phosphorescent material may be directly bound to the backbone of the polymer or spaced apart therefrom by a spacer group, for example a $C_{1-20}$ alkyl spacer group in which one or more non-adjacent C atoms may be replaced by O or S.

The hole-transporting layer as described herein may be non-emissive when the device is in use, or may emit light in which case the hole-transporting layer may contain a light-emitting material as described herein bound to the hole-transporting polymer or mixed with the hole-transporting polymer.

Hole Injection Layers

A conductive hole injection layer, which may be formed from a conductive organic or inorganic material, may be provided between the anode and the light-emitting layer or layers of an OLED to improve hole injection from the anode into the layer or layers of semiconducting polymer. Examples of doped organic hole injection materials include optionally substituted, doped poly(ethylene dioxythiophene) (PEDT), in particular PEDT doped with a charge-balancing polyacid such as polystyrene sulfonate (PSS) as disclosed in EP 0901176 and EP 0947123, polyacrylic acid or a fluorinated sulfonic acid, for example Nafion®; polyaniline as disclosed in U.S. Pat. No. 5,723,873 and U.S. Pat. No. 5,798,170; and optionally substituted polythiophene or poly(thienothiophene). Examples of conductive inorganic materials include transition metal oxides such as VOx MoOx and RuOx as disclosed in Journal of Physics D: Applied Physics (1996), 29(11), 2750-2753.

Where a hole-transporting layer is present, a hole-injection layer may be provided between the anode and the hole-transporting layer.

Charge Transporting and Charge Blocking Layers

A hole transporting layer may be provided between the anode and the light-emitting layer or layers, as described above. Likewise, an electron transporting layer may be provided between the cathode and the light-emitting layer or layers.

Similarly, an electron blocking layer may be provided between the anode and the light-emitting layer and a hole blocking layer may be provided between the cathode and the light-emitting layer. Transporting and blocking layers may be used in combination. Depending on its HOMO and LUMO levels, a single layer may both transport one of holes and electrons and block the other of holes and electrons.

The hole transporting layer preferably has a HOMO level of less than or equal to 5.5 eV, more preferably around 4.8-5.5 eV as measured by cyclic voltammetry. The HOMO level of the hole transport layer may be selected so as to be within 0.2 eV, optionally within 0.1 eV, of an adjacent layer (such as a light-emitting layer) in order to provide a small barrier to hole transport between these layers. The hole-transporting layer may be a polymer comprising repeat units of formula (I) as described above.

If present, an electron transporting layer located between the light-emitting layers and cathode preferably has a LUMO level of around 2.5-3.5 eV as measured by cyclic voltammetry. For example, a layer of a silicon monoxide or silicon dioxide or other thin dielectric layer having thickness in the range of 0.2-2 nm may be provided between the light-emitting layer nearest the cathode and the cathode. HOMO and LUMO levels may be measured using cyclic voltammetry.

An electron transporting layer may contain a polymer comprising a chain of optionally substituted arylene repeat units, such as a chain of fluorene repeat units.

Cathode

The cathode is selected from materials that have a work function allowing injection of electrons into the light-emitting layer. Other factors influence the selection of the cathode such as the possibility of adverse interactions between the cathode and the light-emitting material. The cathode may consist of a single material such as a layer of aluminium. Alternatively, it may comprise a plurality of conductive materials, for example a plurality of conductive metals such a bilayer of a low work function material and a high work function material such as calcium and aluminium as disclosed in WO 98/10621. The cathode may comprise a layer of elemental barium, for example as disclosed in WO 98/57381, Appl. Phys. Lett. 2002, 81(4), 634 and WO 02/84759. The cathode may comprise a thin (e.g. less than 5 nm) layer of metal compound between the organic semi-conducting layers and one or more conductive cathode layers, in particular an oxide or fluoride of an alkali or alkali earth metal, to assist electron injection, for example lithium fluoride, for example as disclosed in WO 00/48258; barium fluoride, for example as disclosed in Appl. Phys. Lett. 2001, 79(5), 2001; and barium oxide. In order to provide efficient injection of electrons into the device, the cathode preferably has a work function of less than 3.5 eV, more preferably less than 3.2 eV, most preferably less than 3 eV. Work functions of metals can be found in, for example, Michaelson, J. Appl. Phys. 48(11), 4729, 1977.

The cathode may be opaque or transparent. Transparent cathodes are particularly advantageous for active matrix devices because emission through a transparent anode in such devices is at least partially blocked by drive circuitry located underneath the emissive pixels. A transparent cathode comprises a layer of an electron injecting material that is sufficiently thin to be transparent. Typically, the lateral conductivity of this layer will be low as a result of its thinness. In this case, the layer of electron injecting material is used in combination with a thicker layer of transparent conducting material such as indium tin oxide.

It will be appreciated that a transparent cathode device need not have a transparent anode (unless, of course, a fully transparent device is desired), and so the transparent anode used for bottom-emitting devices may be replaced or supplemented with a layer of reflective material such as a layer of aluminium. Examples of transparent cathode devices are disclosed in, for example, GB 2348316.

Encapsulation

Organic optoelectronic devices tend to be sensitive to moisture and oxygen. Accordingly, the substrate preferably has good barrier properties for prevention of ingress of moisture and oxygen into the device. The substrate is commonly glass, however alternative substrates may be used, in particular where flexibility of the device is desirable. For example, the substrate may comprise one or more plastic layers, for example a substrate of alternating plastic and dielectric barrier layers or a laminate of thin glass and plastic.

The device may be encapsulated with an encapsulant (not shown) to prevent ingress of moisture and oxygen. Suitable encapsulants include a sheet of glass, films having suitable barrier properties such as silicon dioxide, silicon monoxide, silicon nitride or alternating stacks of polymer and dielectric or an airtight container. In the case of a transparent cathode device, a transparent encapsulating layer such as silicon monoxide or silicon dioxide may be deposited to micron levels of thickness, although in one preferred embodiment the thickness of such a layer is in the range of 20-300 nm. A getter material for absorption of any atmospheric moisture and/or oxygen that may permeate through the substrate or encapsulant may be disposed between the substrate and the encapsulant.

Formulation Processing

A formulation suitable for forming the hole-transporting layer and the light-emitting layer may be formed from the components forming those layers and one or more suitable solvents.

The formulation may be a solution of the components of the layer in question, or may be a dispersion in the one or more solvents in which one or more components are not dissolved. Preferably, the formulation is a solution.

Particularly preferred solution deposition techniques including printing and coating techniques such spin-coating and inkjet printing.

Coating methods are particularly suitable for devices wherein patterning of the light-emitting layer is unnecessary—for example for lighting applications or simple monochrome segmented displays.

Printing methods are particularly suitable for high information content displays, in particular full colour displays. A device may be inkjet printed by providing a patterned layer over the anode and defining wells for printing of one colour (in the case of a monochrome device) or multiple colours (in the case of a multicolour, in particular full colour device). The patterned layer is typically a layer of photoresist that is patterned to define wells as described in, for example, EP 0880303.

As an alternative to wells, the ink may be printed into channels defined within a patterned layer. In particular, the photoresist may be patterned to form channels which, unlike wells, extend over a plurality of pixels and which may be closed or open at the channel ends.

Other solution deposition techniques include dip-coating, slot die coating, roll printing and screen printing.

For the avoidance of doubt, insofar as is practicable any embodiment or aspect of the invention may occur in combination with any other embodiment or aspect of the invention.

EXAMPLE

Comparative Hole-Transporting Polymer

A hole-transporting polymer was formed by Suzuki polymerisation as described in WO 00/53656 comprising:
  50 mol % of a repeat unit of formula (XIa) wherein $R^7$ is methyl in each case, d=1 in each case and $R^8$ is a substituent as described in the description;
  40 mol % of a repeat unit of formula (V) sub-formula 1 wherein the central $Ar^9$ group linked to two N atoms is substituted fluorene and $Ar^{10}$ is phenyl in both occurrences and the remaining Ar groups are phenylene as described in the description.

10 mol % of a crosslinkable repeat unit of formula (XIa).

The average repeat unit molecular weight of the polymer is about 600 Da.

Figure 2:
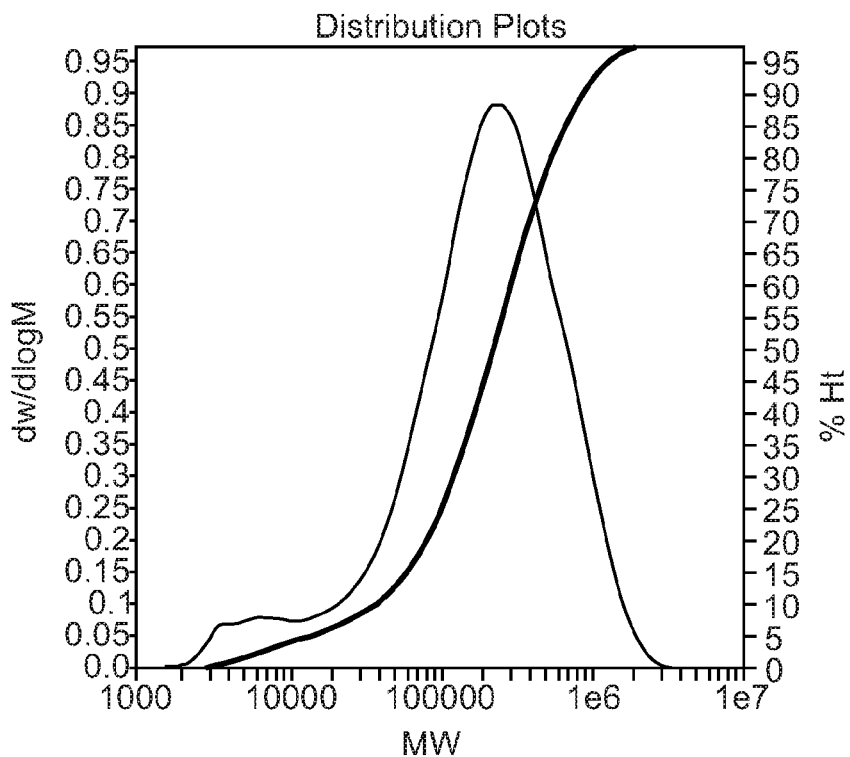
FIG. 2 illustrates a polystyrene equivalent molecular weight distribution plot measured by gel permeation chromatography of a hole-transporting polymer as described in the Comparative Example and a cumulative height for this distribution.
Figure 4:
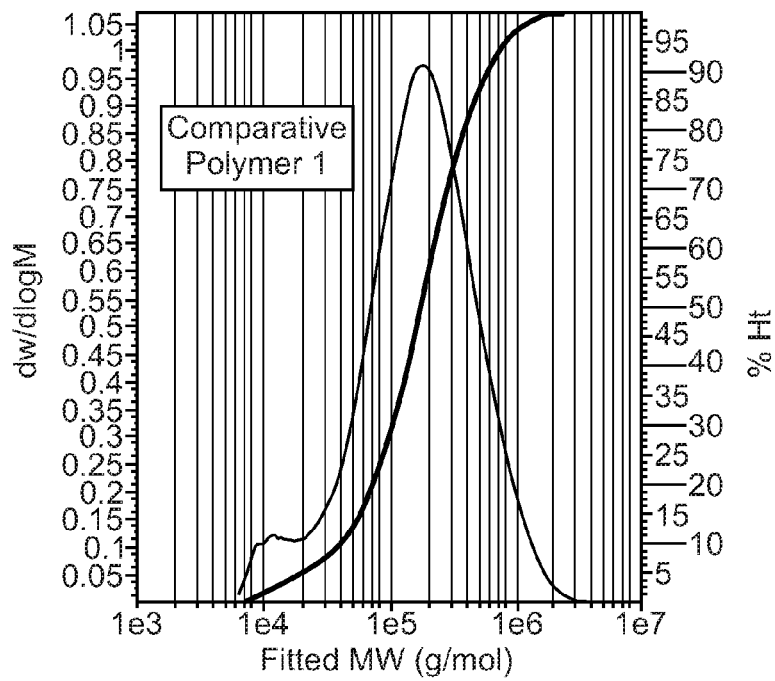
FIG. 4 illustrates an absolute molecular weight distribution plot measured by triple detection gel permeation chromatography of a hole-transporting polymer as described in the Comparative Example and a cumulative height for this distribution.

The polymer was analysed by gel permeation chromatography and the polystyrene-equivalent weight-average molecular weight (Mw) of the polymer was 317,000, the polystyrene-equivalent number-average molecular weight (Mn) was 55,000 and the polystyrene-equivalent polydispersity index was 5.7. A polystyrene equivalent weight distribution plot of this polymer measured by gel permeation chromatography is shown in FIG. 2. An absolute molecular weight distribution plot of this polymer measured by triple detection gel permeation chromatography is shown in FIG. 4

Hole-Transporting Polymer Example 1

The comparative polymer described in the example above was fractionated by selective precipitation. The comparative polymer was dissolved in toluene and added dropwise to isopropyl alcohol. The resultant solid or gel was separated from the solvents and the process was repeated a further two times to provide a polymer with optimised molecular weight distributions.

Figure 3:
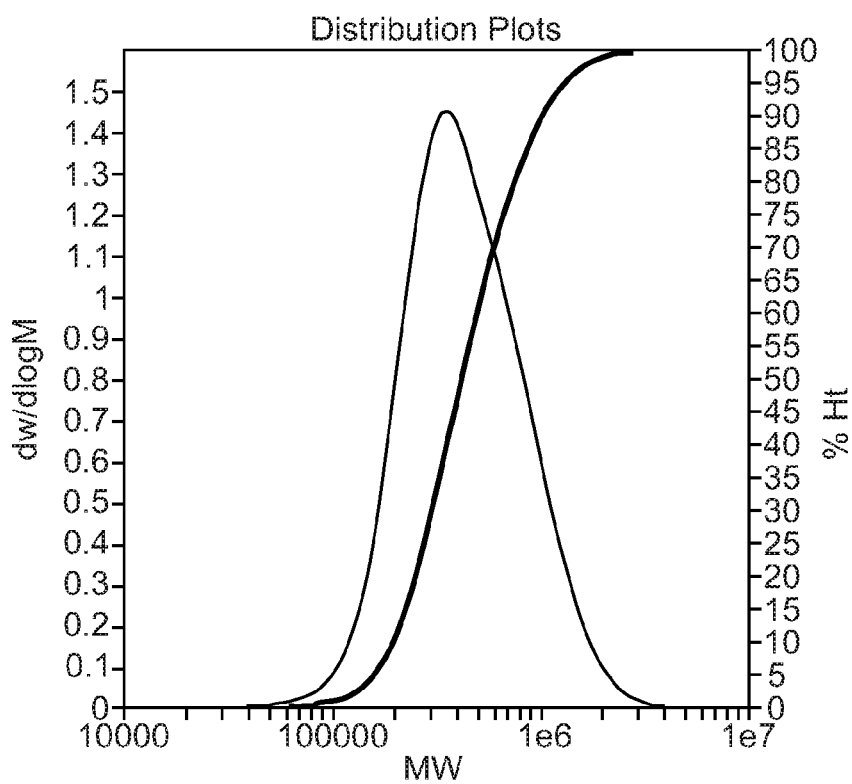
FIG. 3 illustrates a polystyrene equivalent molecular weight distribution plot measured by gel permeation chromatography of a hole-transporting polymer as described in Example 1 and a cumulative height for this distribution.
Figure 5:
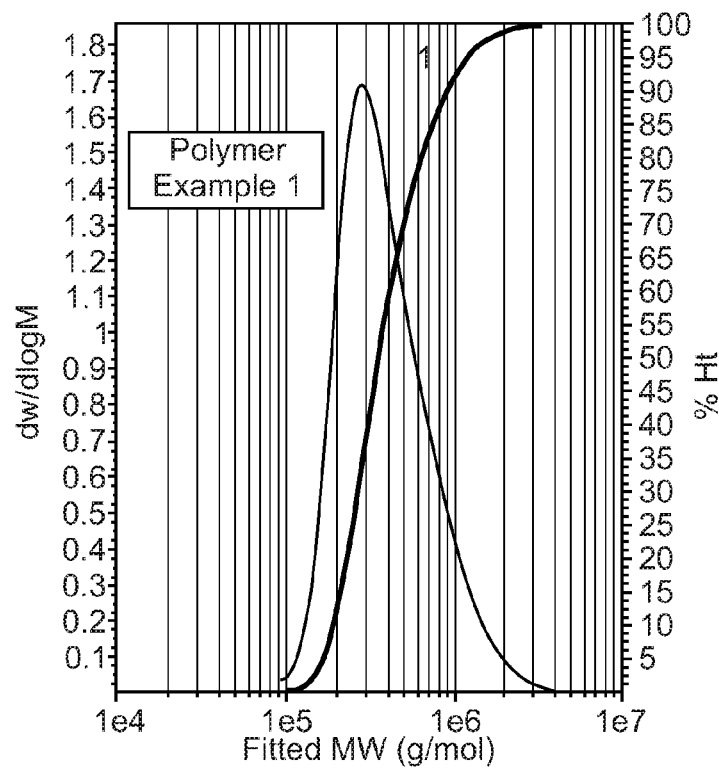
FIG. 5 illustrates an absolute molecular weight distribution plot measured by triple detection gel permeation chromatography of a hole-transporting polymer as described in Example 1 and a cumulative height for this distribution.
Figure 6:
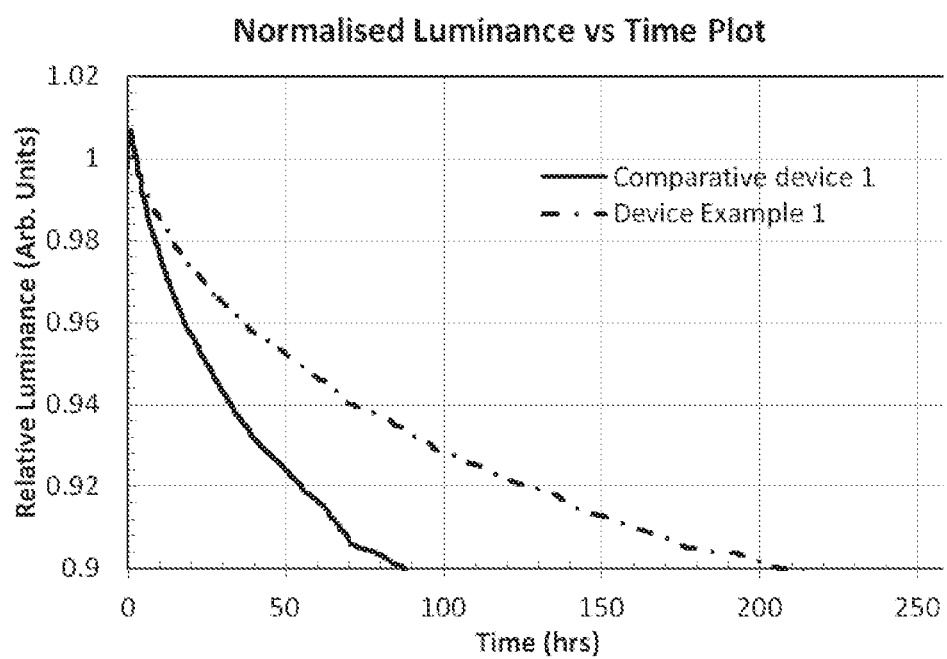
FIG. 6 illustrates a normalised luminance vs time plot comparing Comparative Device 1 containing a hole-transporting layer formed from the Comparative Example polymer and Device Example 1 containing a hole-transporting layer formed from the polymer of Example 1

The polymer was analysed by gel permeation chromatography and the polystyrene-equivalent weight-average molecular weight (Mw) of the polymer was 523,000, the polystyrene-equivalent number-average molecular weight (Mn) was 350,000 and the polystyrene-equivalent polydispersity index was 1.5. A polystyrene equivalent weight distribution plot of this polymer measured by gel permeation chromatography is shown in FIG. 3. An absolute molecular weight distribution plot of this polymer measured by triple detection gel permeation chromatography is shown in FIG. 5

The proportions by weight of polymer chains making up different polystyrene equivalent molecular weight ranges of the total polymer weight as measured by GPC are set out in Table 1.

Proportions for Comparative Polymer 1 and Polymer Example 1 are taken from the normalised cumulative heights shown in FIGS. 2 and 3 respectively. Height measurements were taken at a data rate of 1 Hz, and summed and normalised using Cirrus software available from Agilent.

TABLE 1

| Molecular weight range | Comparative Polymer 1 Proportion of total polymer weight by GPC (%) | Polymer Example 1 Proportion of total polymer weight by GPC (%) |
| --- | --- | --- |
| <30k | 9.05 | 0 |
| 30-50k | 4.29 | 0.05 |
| 50-100k | 12.45 | 0.78 |
| 100-300k | 37.77 | 29.45 |
| 300-500k | 16.91 | 30.99 |
| 500-1000k | 14.49 | 28.60 |
| >1000k | 5.04 | 10.14 |

The proportions by molecular weight of polymer chains making up different weight ranges of the total polymer weight as measured by triple detection GPC are set out in Table 2.

Proportions for Comparative Polymer 1 and Polymer Example 1 are taken from the normalised cumulative heights shown in FIGS. 4 and 5 respectively. Height measurements were taken at a data rate of 1 Hz, and summed and normalised using Agilent GPC software.

TABLE 2

| Molecular weight range | p/r ratio | Comparative Polymer 1 Proportion of total polymer weight by Triple Detection GPC (%) | Polymer Example 1 Proportion of total polymer weight by Triple Detection GPC (%) |
| --- | --- | --- | --- |
| >1000000 | >~1600 | 2.68 | 7.37 |
| 1000000-500000 | ~1600-830 | 9.89 | 21.87 |
| 500000-300000 | ~830-500 | 14.40 | 30.93 |
| 300000-100000 | ~500-160 | 43.29 | 39.70 |
| 100000-50000 | ~160-80 | 16.73 | 0.13 |
| 50000-30000 | ~80-50 | 5.36 | 0 |
| <30000 | ~50 | 7.66 | 0 |

Comparison of the Hole-Transporting Polymers

The degree of insolubility of polymers was measured using the following method.

A series of solutions of different concentration of the polymer in a solvent were prepared and the absorption of each was measured by UV-VIS spectroscopy to provide a calibration curve. The polymer was then deposited by spin coating onto glass substrates from solution to a thickness of 22 nm as determined by a Dektak profilometer.

One of the substrates was left unbaked and the other was cross-linked by heating at 175° C. for 60 minutes. The cross-linked film was then soaked in a measured volume of solvent for a specified time, after which the solvent was transferred to a cuvette and the absorption spectrum measured by UV-VIS spectroscopy and compared to the calibration curve to determine the concentration of polymer in solution. The non-cross-linked film was treated similarly, which resulted in complete dissolution of the polymer. Measurement of absorption spectrum of this solution of this sample by UV-VIS spectroscopy gave the total amount of polymer present.

The amount of hole-transporting layer that remained insoluble after cross-linking of the comparative hole-transporting polymer and hole-transporting polymer 1 respectively were compared in the table below:

| | % of original material remaining |
| --- | --- |
| Comparative hole-transporting polymer | 80 |
| Hole-transporting polymer example 1 | 100 (at limit of measurement technique) |

Comparative Device

A device having the following structure was prepared:

| ITO/HIL/HTL/LE/Cathode |
| --- |
| ITO/HIL/HTL/LEL/Cathode | wherein ITO is an indium-tin oxide anode; HIL is a hole-injecting layer comprising a hole-injecting material, HTL is a hole-transporting layer, and LEL is a light-emitting layer.

A substrate carrying ITO patterned to form pixel anodes was cleaned using UV/Ozone. A layer of photoresist was deposited over the substrate by spin-coating and patterned to expose the pixel anodes and form wells having the pixel anodes at a base of the wells. A 30 nm hole-injection layer was formed by inkjet printing a hole-injection material into the wells. The hole-transporting layer was formed to a thickness of about 22 nm by inkjet printing a solution of the Comparative Hole-Transporting Polymer and evaporating the solvent. The hole-transporting layer was heated at 170° C. for 1 hour to crosslink the crosslinkable groups of the polymer. A light-emitting layer was formed to a thickness of about 65 nm by inkjet printing a solution of a light-emitting polymer and an additive polymer, the light-emitting polymer comprising fluorene repeat units of formula (XIa), a repeat unit of formula (VIIIa), amine repeat units of formula (Va-1) and (Va-3). The cathode was formed by depositing a layer of sodium fluoride of a thickness of about 2 nm, a layer of silver of about 100 nm thickness and a layer of aluminium of a thickness of about 100 nm.

Device Example 1

A device was prepared as described for the Comparative Device except that hole-transporting polymer example 1 was used in place of the comparative hole-transporting polymer.

Device Example 1 has improved performance compared to the Comparative Device. As shown in FIG. 3, Device Example 1 has an improved device lifetime compared to the Comparative Device.

Although the present invention has been described in terms of specific exemplary embodiments, it will be appreciated that various modifications, alterations and/or combinations of features disclosed herein will be apparent to those skilled in the art without departing from the scope of the invention as set forth in the following claims.

The invention claimed is:

1. An OLED comprising a hole-transporting layer and light-emitting layer, wherein the hole-transporting layer comprises a hole-transporting polymer, wherein no more than 5% of the polystyrene equivalent polymer weight measured by gel permeation chromatography consists of chains with a molecular weight of less than 50,000.

2. The OLED according to claim 1, wherein the hole-transporting layer comprises a hole-transporting polymer, wherein no more than 0.2% of the polystyrene equivalent polymer weight measured by gel permeation chromatography consists of chains with a molecular weight of less than 50,000.

3. The OLED according to claim 1, wherein no more than 10% of the polystyrene equivalent polymer weight measured by gel permeation chromatography consists of polymer chains with a molecular weight of less than 100,000.

4. An OLED comprising a hole-transporting layer and light-emitting layer, wherein the hole-transporting layer comprises a hole-transporting polymer wherein no more than 10% of the polystyrene equivalent polymer weight measured by gel permeation chromatography consists of chains with a molecular weight of less than 100,000.

5. The OLED according to claim 4, wherein no more than 5% of the polystyrene equivalent polymer weight measured by gel permeation chromatography consists of chains with a molecular weight of less than 100,000.

6. The OLED according to claim 1, wherein more than 20% of the polystyrene equivalent polymer weight measured by gel permeation chromatography consists of polymer chains with a molecular weight of at least 300,000.

7. An OLED comprising a hole-transporting layer and light-emitting layer wherein the hole-transporting layer comprises a hole-transporting polymer, wherein no more than 5% of the weight of the polymer as measured by triple detection gel permeation chromatography consists of polymer chains with a p/r ratio of less than about 50 wherein p/r is absolute polymer chain molecular weight/average repeat unit molecular weight.

8. The OLED according to claim 7, wherein less than 1% of the weight of the polymer as measured by triple detection gel permeation chromatography consists of polymer chains with a p/r ratio of less than about 50.

9. The OLED according to claim 7, wherein less than 10%, of the weight of the polymer as measured by triple detection gel permeation chromatography consists of polymer chains with a p/r ratio of less than about 100.

10. The OLED according to claim 7, wherein more than 20% of the weight of the polymer as measured by triple detection gel permeation chromatography consists of polymer chains with a p/r ratio of more than about 500.

11. The OLED according to claim 1, wherein the hole-transporting polymer has a polydispersity index of less than 4.

12. The OLED according to claim 1, wherein the hole-transporting polymer has a number-average molecular weight (Mn) in the range of $1 \times 10^5$ to $1 \times 10^6$.

13. The OLED according to claim 1, wherein the hole-transporting polymer has a weight average molecular weight in the range of $1 \times 10^5$ to $1 \times 10^6$.

14. The OLED according to claim 1, wherein the hole-transporting polymer is crosslinked.

15. The OLED according to claim 14, wherein no more than 25 mol % of the repeat units of the hole-transporting polymer are crosslinking groups.

16. The OLED according to claim 1, wherein the hole-transporting polymer is a conjugated polymer.

17. The OLED according to claim 1, wherein the hole-transporting polymer comprises a repeat unit of formula (V):

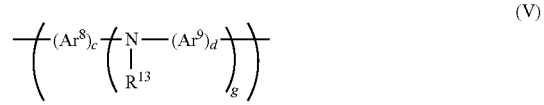

(V)

wherein $Ar^8$ and $Ar^9$ in each occurrence are independently substituted or unsubstituted aryl or heteroaryl, g is greater than or equal to 1, $R^{13}$ is H or a substituent, and c and d are each independently 1, 2, or 3.

18. The OLED according to claim 1, wherein the hole-transporting polymer is a fractionated polymer.

19. A process for the preparation of an OLED according to claim 1, comprising the steps of:
 (i) forming a hole-transporting layer which comprises the hole-transporting polymer; and
 (ii) forming a light-emitting layer over the hole transporting layer, wherein the light-emitting layer is formed by depositing a formulation comprising the material or materials of said layer and at least one solvent, and evaporating the at least one solvent.

20. The process according to claim 19, wherein the hole-transporting layer is formed by depositing a formulation comprising the material or materials of said layer and at least one solvent, and evaporating the at least one solvent.

21. The process according to claim 20, wherein the hole-transporting polymer is soluble in one or more solvents used in step (ii) in forming the light-emitting layer.

22. The process according to claim 19, wherein the hole-transporting layer is crosslinked prior to formation of the light-emitting layer.

* * * * *